United States Patent
Silva et al.

(10) Patent No.: US 9,603,556 B2
(45) Date of Patent: Mar. 28, 2017

(54) DEVICE AND METHOD FOR CONTINUOUS BIOMETRIC RECOGNITION BASED ON ELECTROCARDIOGRAPHIC SIGNALS

(71) Applicants: INSTITUTO SUPERIOR TECNICO, Lisbon (PT); INSTITUTO DE TELECOMUNICAÇÕES, Lisbon (PT); INSTITUTO SUPERIOR DE ENGENHARIA DE LISBOA, Lisbon (PT)

(72) Inventors: Hugo Humberto Plácido da Silva, Lisbon (PT); André Ribeiro Lourenço, Odivelas (PT); Ana Luísa Nobre Fred, Lisbon (PT)

(73) Assignees: INSTITUTO SUPERIOR TECNICO, Lisbon (PT); INSTITUTO DE TELECOMUNICAÇÕES, Lisbon (PT); INSTITUTO SUPERIOR DE ENGENHARIA DE LISBOA, Lisbon (PT)

( * ) Notice: Subject to any disclaimer, the term of this patent is extended or adjusted under 35 U.S.C. 154(b) by 122 days.

(21) Appl. No.: 14/373,099

(22) PCT Filed: Jan. 14, 2013

(86) PCT No.: PCT/PT2013/000002
§ 371 (c)(1),
(2) Date: Jul. 18, 2014

(87) PCT Pub. No.: WO2013/109154
PCT Pub. Date: Jul. 25, 2013

(65) Prior Publication Data
US 2014/0361871 A1 Dec. 11, 2014

(30) Foreign Application Priority Data
Jan. 19, 2012 (PT) ........................................ 106102

(51) Int. Cl.
*A61B 5/117* (2016.01)
*A61B 5/00* (2006.01)
(Continued)

(52) U.S. Cl.
CPC ............ *A61B 5/117* (2013.01); *A61B 5/0402* (2013.01); *A61B 5/04012* (2013.01);
(Continued)

(58) Field of Classification Search
CPC . A61B 5/04012; A61B 5/0402; A61B 5/0002; A61B 5/0205; A61B 5/0408; G06K 2009/00939; G06K 9/00885; G06K 9/00496
(Continued)

(56) References Cited

U.S. PATENT DOCUMENTS

| 6,898,299 B1 * | 5/2005 | Brooks | G06K 9/00 340/5.52 |
| 2006/0136173 A1 * | 6/2006 | Case | A63B 24/00 702/182 |

(Continued)

FOREIGN PATENT DOCUMENTS

WO 2009/112983 A1 9/2009

OTHER PUBLICATIONS

International Search Report for PCT/PT2013/000002 filed Jan. 14, 2013.
(Continued)

*Primary Examiner* — Mirza Alam
(74) *Attorney, Agent, or Firm* — Porzio, Bromberg & Newman, P.C.

(57) ABSTRACT

Signal measurement for biometric recognition purpose includes a computational unit and a sensory unit designed to measure electrocardiographic (ECG) signals in a continuous fashion, guaranteeing that the biometric recognition is per-
(Continued)

formed in an uninterrupted way whenever the device is used, with the purpose of enabling the automated recognition or validation of the identity of its wearer. The sensory unit has an electronic module through which the ECG is acquired. Its operating principle can be based in the electrical conductivity, in which case it requires contact with the skin of the user, or in any kind of capacitive or mechanical element, in which case it does not require any direct contact with the user. The device can be used in alternative or as a complement to existing systems that only perform a momentary identity check. It can be applied to vehicles, tablet computers or analogous contexts.

10 Claims, 7 Drawing Sheets

(51) Int. Cl.
    *A61B 5/0402*    (2006.01)
    *G06K 9/00*    (2006.01)
    *A61B 5/04*    (2006.01)
    *G07C 9/00*    (2006.01)

(52) U.S. Cl.
    CPC .......... *A61B 5/6893* (2013.01); *A61B 5/6895* (2013.01); *A61B 5/6898* (2013.01); *G06K 9/00885* (2013.01); *G07C 9/00158* (2013.01); *F04C 2270/041* (2013.01); *G06K 2009/00939* (2013.01)

(58) Field of Classification Search
    USPC .............................. 340/5.52, 5.82; 700/150
    See application file for complete search history.

(56) References Cited

U.S. PATENT DOCUMENTS

| | | | |
|---|---|---|---|
| 2006/0215883 A1* | 9/2006 | Kim | G06K 9/00496 382/115 |
| 2008/0228046 A1 | 9/2008 | Futatsuyama et al. | |
| 2009/0009284 A1* | 1/2009 | Sako | G06F 19/3481 340/5.82 |
| 2009/0234552 A1* | 9/2009 | Takeda | B60W 30/16 701/96 |
| 2011/0254662 A1* | 10/2011 | Lindsay | G06F 19/322 340/5.82 |
| 2011/0260830 A1* | 10/2011 | Weising | G06F 3/015 340/5.52 |
| 2012/0004523 A1 | 1/2012 | Richter | |

OTHER PUBLICATIONS

Hugo Silva et al: "Study and Evaluation 1-12 of a Single Differential Sensor Design Based on Electro-textile Electrodes for ECG Biometrics Applications", 2011 IEEE Sensors Proceedings: Limerick, Ireland, IEEE, Piscataway, NJ, Oct. 2011 , pp. 1764-1767.
Yama Y et al: "Development of a Wireless Capacitive Sensor for Ambulatory ECG Monitoring over Clothes", 2007 Annual International Conference of the IEEE Engineering in Medicine and Bio Logy Society : [EMBC '07] ; Lyon, France, August 2007.

* cited by examiner

DEVICE AND METHOD FOR CONTINUOUS BIOMETRIC RECOGNITION BASED ON ELECTROCARDIOGRAPHIC SIGNALS

FIELD OF THE INVENTION

Technical Domain of the Invention

The present invention refers to a device composed by a computational unit (206) and a sensory unit (205), for the measurement of electrocardiographic (ECG) signals, with the purpose of performing the biometric recognition of its user in a continuous fashion, even though it can perform the same function momentarily, in the same way performed by other biometric devices.

The computational unit (206) can be any type of electronic equipment suitable for the digital processing and presentation of signals, which includes the central console of a vehicle, portable electronic devices such as a tablet computer, a mobile phone, or analogous devices. This computational unit (206) implements a method which makes it behave in a specific way, allowing the extraction of representative information from the ECG signals collected in real time from the user and/or his biometric recognition. The computational unit (206) also includes a method for customizing its definitions according to the result of the biometric recognition of the user.

State-of-the-Art

Identification and authentication methods have evolved from paradigms based on information that the user knows (e.g. passwords, PIN's, etc.), to paradigms based on objects that the user has (e.g. keys, access cards, etc.), evolving, more recently, to methods based in physiological properties of the user, such as, fingerprint, iris, hand geometry, among others.

The former are generally framed in the field of biometric recognition, which in the current state-of-the-art include different types of biometric and behavioral traits, such as speech recognition, signature, keystroke dynamics, and the Electrocardiogram (ECG). All of these are traits that can be acquired throughout time and that are (at least partially), based on the behavior of the user.

Most of these biometric traits are only suitable for a single and momentary validation, bound to an instant or short period of time, and requiring the user to switch from the tasks he would regular perform. For example, techniques based on the fingerprint and/or hand geometry require the user to place or pass his finger (in some cases even the whole hand), through a physical reader; in the case of techniques based on the iris, the user has to stand in a specific physical space and have is eye in close contact or in line of sight with the reader.

In a continuous biometric recognition perspective, the current methods distract the user and require him to stop the tasks at hands. Therefore, the state-of-the-art has focused on searching for alternative biometric solutions, the Electrocardiogram (ECG) being one of the modalities showing the most promising results.

On ECG signals, each cardiac cycle is composed by a chain of biomechanical events (P-QRS-T), triggered by a bioelectrical activation signal inflicted on the cardiac muscle. This signal is produced by an element of the cardiac system known as sinoatrial node, which is controlled by the autonomic nervous system, and works as a natural pacemaker.

The ECG is a representation of the electrical activity of the heart captured, in general, externally through electrodes applied on the body surface or its vicinity. What the ECG records is the variation of the electrical activity of the heart throughout the cardiac muscle fibers. These electrical changes can be detected using different physical principles, the most common being based in the electrical potential difference between multiple derivations, using several electrical terminal of metallic base, scattered through different parts of the body. Other measurement principles include capacitive and mechanical methods that may not require direct contact with the body. The measurement through mechanical methods can be performed using piezoelectric sensors, accelerometers, pressure sensors or others.

In a normal clinical-grade ECG record, the electrical potential differences are measured in twelve different derivations, with sensor leads scattered throughout the body, including the chest. Recent work has shown that for biometric applications, a single derivation suffices. Still, conventional signal acquisition methods use chest-mounted terminals, gelled metallic electrodes, and bulky measurement equipment. The acceptance of the ECG as a biometric modality has therefore lead the research towards the creation of less intrusive setups, using the hands as signal acquisition points.

As a biometric trait, the ECG signals possess several highly appealing properties, since they provide intrinsic aliveness detection and have a unique potential for continuous biometrics applications, as a complement or alternative to techniques that only allow momentary biometric verification. Depending on the configuration of the sensory unit (205), the ECG signals can be acquired uninterruptedly without interfering with the regular activities of the user, this being the main acceptance challenge for ECG biometrics.

An example of the overreach of ECG signals for identification can be found in the paper "Development of an ECG Identification System", published in 2001 by Kyoso et al. [1]. Biel et al. also shown the feasibility of these signals in a paper from the same year entitled "ECG Analysis: A New Approach in Human Identification" [2]. Both these papers are targeted at identity verification in a momentary fashion, with the proposed methods being based in offline signal processing techniques and data collected through clinical-grade systems using gelled metallic electrodes applied to the trunk of the users.

In a paper from 2011 entitled "Unveiling the Biometric Potential of Finger-Based ECG Signals" [3], the inventors have proposed a measurement method that allows the acquisition of ECG signals at the hands using three metallic electrodes in direct contact with the skin of the user. This approach already presents several advantages when compared to previous work; still, the proposed method is targeted at momentary verification and offline processing of the signal.

In another paper from the same year entitled "Clinical Data Privacy and Customization via Biometrics Based on ECG Signals" [4], the inventors proposed an application of the method described in the previous publication, to the context of clinical data protection. This approach already presents advantages when compared to previous work, but again, the proposed method is targeted at momentary verification and offline processing of the signal.

Still in 2011, in a paper entitled "Study and Evaluation of a Single Differential Sensor Design Based on Electro-textile Electrodes for ECG Biometrics Applications" [5], the inventors performed a comparison of metallic electrodes with conductive lycras. This work has shown the possibility of acquiring the signals of interest for biometric applications through conductive textiles, in opposition to the traditional metallic and gelled electrodes.

Sriram et al. published a paper entitled "Activity-aware ECG-based Patient Authentication for Remote Health Monitoring" [6], where they confirm the validity of ECG signals for biometric purposes. Again, in their work sensors are applied to the chest, although the advantage in this case is that the use of gel is optional. Besides, as in the previous examples, the adopted method is targeted at offline signal processing and momentary identity verification.

Also in terms of patents, there are several examples of ECG based systems. The patent EP0752143B2 by David Osten et al. and published in 1997, describes a system composed by storage, two levels of identity recognition and two levels of identity comparison, which depend on the measurement of multiple parameters in a synchronous way, the fingerprint being described as the preferred modality and combined with pulse wave and ECG recording synchronized in time. The system was designed for application to a counter top and requires the user to input an identification code afterwards. In another patent, with the number US2006215883A1, a method based on neural networks and the Fourier transform is described for momentary identification of the user.

The patent US2008056540A1, by Sachin Vadodaria et al., published in 2008, describes a biometric scanner integrated in a clinical diagnostic system in which the biometric information is collected through traditional modalities such as the fingerprint, retina, and voice, also showing the dependency on additional credentials for authentication. Furthermore, the authentication scenario is the only one contemplated in this invention, and the acquisition of electrophysiological and hemodynamic signals is dependent on the cabled link between two clinical-grade systems (from General Electrics), where we assume the dependency on gelled metallic electrodes. In another patent published in 2008, with the number US2009009284A1, and proposed by Yoichiro Sako, the inventors describe an information sharing method through a network connection, in which the signals are collected from a device applied to the body of the user.

An application of several signals in the context of a vehicle, where the ECG is referred as an accessory modality can be found in the patent US2009234552A1. In this case, published in 2009 and in which the inventors are Kazuya Takeda et al., a system for driver behavior modeling is proposed, in which the identification aspect is not addressed and mostly information from the vehicle dynamics and its surrounding is used.

In the patent US2011254662A1 published in 2011, the inventor Noel Lindsay focuses on the use of Holter-type devices, with metallic electrodes applied to several point on the chest of the user, to collect ECG signals in an ambulatory setting and use them for biometric identification of the user. Another patent, US2011260830A1 by George Weising and published in 2011, discloses the use of ECG signals collected from metallic electrodes in contact with the user and integrated in a video game controller for identification of the user in a multimedia interaction.

All of these references do not represent prior art or analogous work, but further reinforce the interest, usefulness, and topical novelty of the aspects presented in our invention. The proposed invention overcomes in an innovative and inventive way, several limitations found in existing biometric recognition systems, in particular, our invention is particularly advantageous since it depends on a single parameter (the ECG) and enables the continuous identification of the user through an integrated system that collects the data using methods that do not require direct contact with the subject or that do not require metallic electrodes. Another particularly advantageous feature is that our sensory module uses a virtual ground in the embodiments that require direct contact with the user, enabling the use of only two contact points with the subject.

The invention also discloses several preferred embodiments that are inventive in nature and are not addressed by previous work, namely the identification in tablet computers through contactless sensors, the identification of drivers using signals collected through non-metallic sensors integrated in a steering wheel and/or contactless sensors integrated in the seat, the identification of motorcycle riders using signals collected through non-metallic sensors integrated in the handlebars of the motorcycle and/or contactless sensors integrated in the seat, and the identification of athletes while operating a gym machine using non-metallic sensors and/or contactless sensors integrated in it. In particular, in contexts where the user is subjected to intense motion, and where the device is exposed to strong electromagnetic noise, such as a vehicle or gym machine, the state-of-the-art exhibits strong limitations, without being obvious the applicability of existing methods nor the quality of the collected signals in those scenarios for biometric recognition purposes.

To illustrate some of the advantages of the proposed invention, in one of the preferred embodiments, the invention is materialized as a device for continuous biometric recognition based in electrocardiographic signals inside the cabin of a car, allowing the identification or authentication of the driver. In another preferred embodiment, the sensory unit (205) is integrated in the motherboard of a tablet computer.

SUMMARY OF THE INVENTION

The present invention refers to a computational unit (206) and a sensory unit (205), together referred to as the device, and which are targeted at the measurement of Electrocardiographic (ECG) signals in a continuous fashion, with the purpose of enabling the recognition or validation of the identity of its user.

The device is especially designed for continuous verification of identity in vehicles and tablet computers, guaranteeing that the biometric recognition occurs uninterruptedly during the time in which the device is worn by the user, although it can also perform the same functions momentarily, in an analogous way to that of other biometric devices.
Sensory Unit The sensory unit (205) comprises the electronic modules of: measurement terminals (201) to interface with the user; transduction and signal conditioning with virtual ground (202); analog-to-digital conversion (203) and signal transmission (204). The first two modules can also be together referred to as sensor.

The interface with the user is performed through one or more electronic modules of measurement terminals (201), through which the ECG signal trace is acquired. Depending on the operating principle of the sensor, this module can be in direct contact with any part of the user's body or not. The hand palms, in particular the thenar eminence, are the preferential application point in the case where contact is needed. The back of the trunk and buttocks, are the preferred zones in the vicinity of which the module is placed in the contactless case.

The electronic module of transduction and signal conditioning with virtual ground (202), performs the conversion and detection of the physical quantity through the electronic module of measurement terminals (201), filters the resulting signal, and amplifies it so that it can be treated as an electrical quantity. The electronic module of transduction and signal conditioning with virtual ground (202) includes an electromagnetic noise filter, compatible with the transmission of the signals through a wireless connection. As a result of the operation of this module, the electrical quantity is a clean and high definition representation of the physical quantity, free of external noise.

The electronic module of analog-to-digital conversion (203) transforms the electrical quantity, obtained through the electronic module of transduction and signal conditioning with virtual ground (202), in an adequate digital representation manageable in the computational unit (206). The virtual ground is generated by an electronic circuit and provides a reference voltage to the instrumentation amplifiers, enabling the use of just two measurement terminals and eliminating the need for the third electrode (real ground), indispensable for the acquisition of the signal using traditional measurement devices.

The electronic module of signal transmission (204) has the purpose of sending the digital representation generated by the electronic module of transduction and signal conditioning with virtual ground (202) to the computational unit (206). This process can be performed using a cabled or wireless link, or even be performed through electrical tracks in a printed circuit board.

Computational Unit

The computational unit (206) can be any electronic equipment suitable for digital signal processing, including the central processing unit of electronic devices such as tablet computers (401), the central console of a car (301), the central console of a motorcycle (501), or the central console of a gym machine (601). The computational unit (206) can also have any equipment for graphical presentation and representation of both the signals and the result of the recognition process, including electronic devices such as the graphical representation screen of a tablet computer (402), the screen on the central console of a car (302), the screen on the central console of a motorcycle (502), or the screen on the central console of a gym machine (602). This computational unit (206) implements a method that shapes the way in which it operates, enabling the extraction of representative information from the ECG signals collected from the user of the device, the corresponding biometric recognition, and the production of a technical effect according to the produced decision. This process is preferentially performed in a continuous fashion that is, ensuring that the biometric recognition occurs uninterruptedly while the device is being used, although it can also be performed in a momentary way. The computational unit (206) is also characterized in that it includes a method for customization of its settings as a result of the biometric recognition of the user.

DETAILED DESCRIPTION OF THE INVENTION

As previously described, the device in this invention comprises a sensory unit (205) and a computational unit (206), which will be further detailed in this section. The computational unit (206) can be an electronic device of any kind, that changes its behavior, appearance, settings and properties, according to the output of a method that it implements, and that uses the ECG signals collected from the sensory unit (205) and processes them in order to produce a decision about the biometric recognition and identity of the user.

The electronic module of measurement terminals (201) from the sensory unit (205) can be directly integrated in it, although alternatively, it can also consist of independent leads, connected to the remaining modules of the sensory unit (205) through wires or cables with variable length, in order to facilitate the construction of its embodiment.

The sensory unit (205) can be based in different operating principles, namely, in the electrical potential difference measured between the terminals, in which case it requires contact with the skin of the user of the device, or, alternatively, it can also be based on the changes in the electromagnetic field measured using a capacitive element, or yet, by measuring the mechanical action of any type, in which cases it may not require direct contact with the user of the device. The measurement through the mechanical action can be performed through piezoelectric, acceleration, or pressure sensors, among others.

When direct contact with the user is required, that contact is preferentially made through non-metallic elements, such as conductive coatings, films, conductive tapes or other materials that eliminate the need to use any kind of metallic element and conductive gel or paste. For example, in one of its preferred embodiments, the sensor has an electronic module of measurement terminals (201) which is composed by conductive coatings or films, which without requiring the use of conductive gel or paste for a good interface with the skin, enable the measurement of the ECG signal between the two hand (at the fingers or hand palms).

The measurement is performed using an electronic module of signal transduction and conditioning with virtual ground (202). In the present invention, this module is designed in a particularly advantageous way for the case where direct contact with the user of the device is needed, since there is a circuit that produces a virtual reference voltage, allowing the use of just two measurement terminals, and eliminating the need for the traditional third electrode that collects the real ground, indispensable for the signal acquisition using traditional methods. The electronic module of signal transduction and conditioning with virtual ground (202) performs the filtering and amplification of the signal, producing a more suitable representation of the physical quantity. The filtering type is band pass, being particularly advantageous in the present invention which, by having a passing band between 0.5 and 40 Hz, eliminates the need for the traditional notch filters, allowing an adequate separation between the ECG signal and parasite signals such as motion artifacts, baseline wander, muscle signals, power line interference, among others. The amplification has a gain between 10 and 10000, allowing the increase in the definition of the collected signal (in the order of uV, mV or V), making the tenuous ECG signals more immune to external noise, and enabling a sufficient definition for the biometric recognition method to operate.

The physical placement of this module with respect to the electronic module of measurement terminals (201) is also particularly advantageous in the invention. Although several other configurations are admissible in the context of the invention, the placement of this module near the point of interface with the user greatly minimizes the appearance of parasite signals. In the traditional signal acquisition methods, this module is placed away from the point of interface with the user, making the cabled connection work as an antenna that captures several surrounding noise sources.

The electronic module of analog-to-digital conversion (203), which transforms the conditioned electrical quantity into a digital representation manageable in the computational device (206), integrates a quantization element and an analog-to-digital converter. The quantization element is a component that maps the voltage or current to a set of bits (also known as resolution), which in the case of the present invention is comprehended between 8 and 64 bits. The analog-to-digital converter is a component that, at regular and pre-defined time intervals, collects a sample, which is then quantized. In the case of the present invention, the frequency at which the samples are collected (sampling rate) can range between 250 Hz and 4 kHz, which in samples collected per unit of time corresponds respectively to 250 and 4000 samples per second.

The electronic module of signal transmission (204) is capable of sending the acquired ECG signals to the computational unit (206) using several methods. In this domain the present invention is particularly advantageous since it can use a wireless channel using existing protocols such as Bluetooth, WiFi, ZigBee or ANT, although other protocols can also be admissible.

Alternatively, the transmission can also be performed in a cabled manner, which in the present invention is also advantageous since it can be performed through the CAN-BUS (Controller Area Network Bus) that allows the internal communication within a vehicle, although more conventional interfaces can also be used, such as USB, COM/RS232, GPIO pins, tracks in a printed circuit board, direct connection to the Rx/Tx pins on a micro controller, and others.

As a whole, the embodiment of the device is such that the sensory unit (205) and the computational unit (206) are integrated in one another. For example, we consider a preferred embodiment of the invention to be a tablet computer, which integrates the sensory unit (205) and implements the method which makes it behave in a different way, enabling the extraction of meaningful information from the ECG signals collected from the user and perform his biometric recognition.

In any case, by reasons related with the convenience of application and use of the device other configurations are more suitable, other embodiments of the sensory unit (205) are also admissible, in which the sensory unit (205) and the computational unit (206) are detached from one another, but where the electronic module of signal transmission (204) from the sensory unit (205) ensures the communication between both. For example, we consider a preferential embodiment of this invention to be the combination of a steering wheel that integrated the sensory unit (205) and transmits the ECG signals through the CAN bus of the vehicle, and its central console, which in this case serves also as the computation unit (206) of the device.

The previously described examples should not limit the scope of the invention, in particular in what concerns the computational unit (206), since this can assume different formats, which include dedicated hardware, specifically created for the implementation of the biometric recognition method, but that can also take advantage of already existing hardware such as portable electronic devices, portable computers, desktop computers, the central console of a vehicle, a watch, a computer screen, or any other device designed for human-machine or machine-machine interaction.

The biometric recognition assumes that the user is enrolled in a database of known users. This enrollment is initially performed using the sensory unit (205). The computational unit (206) either integrates a database of known users, or communicates with a central server that stores that information remotely. To decide on the biometric recognition of the user, in particular, about granting or rejecting his access, there is a method in charge of handling the data, which collects the information transmitted by the sensory unit (205), and produces a decision on granting or denying access to the system.

The biometric recognition method used in the present invention is particularly advantageous given that it can produce a decision on the identification or authentication of the user in a continuous fashion, that is, guaranteeing that the biometric recognition occurs uninterruptedly during the time in which the user interacts with the device, or just upon request, that is, in a momentary away, where the recognition is spaced in time by several minutes, hours, or days. The method applies a set of pattern recognition and knowledge discovery algorithms, which use the ECG signals collected by the sensory unit (205), in raw form or as an alternative representation generated from the representative information extracted from them, and that matches the resulting information with the patterns previously stored in the enrolled users database.

This process is composed by a first stage in which the signal received from the sensory unit (205) is pre-processed, a second stage where the representative information is extracted, and a final stage of classification, where a decision is produced. In the pre-processing stage, an additional digital filtering step is implemented which complements those performed in the sensory unit (205). The representative information extraction stage performs the segmentation of the ECG waveform and its different complexes (P-QRS-T), or, in alternative, just a few complexes are segmented for improved efficiency (RS-T). This last way of segmentation is particularly advantageous in this invention, since it allows a more accurate detection of the events of interest in the heartbeat waveform, being at the same time highly efficient in terms of processing as it is only based in data accessed in real-time and not on past information (as in the cases where the P complex needs to be detected).

Representative information about the complexes can also be extracted for each user, such as latencies and amplitudes (PQ segment, ST segment, among others); furthermore, the average of several heartbeat waveforms or of the extracted information can also be used. These are also particularly advantageous properties of the present invention.

The classification stage compares the representative information with the data collected during the enrollment, to determine or validate the identity of the user using a nearest neighbor (k-NN) approach with Euclidean distance as similarity metric, or, alternatively, use Support Vector Machines (SVM). Still, other classification methods are admissible in the context of the present invention.

Finally, a decision about the biometric recognition of the user is produced in the computational unit (206).

The result produced by the computational unit (206) can have different technical effects, which include but are not limited to: the identification of the user of the device, the verification of the identity of the user of the device, detection of impostors, presentation of the decision to the user, granting or inhibiting the access to digital contents (e.g. login to the device, payments, access to Internet websites, among others) or to physical resources (e.g. buildings, rooms, vehicles, security safes, among others), customization of a device (e.g. car, motorcycle, gym machine, tablet computer, among others). The device is particularly advantageous for the purpose for which it is designed, since it allows the simultaneous detection of the hands in the sensor or the proximity of the user to the device, aliveness detection, and the connection or relaying of control signals to other devices and accessories to generate a technical effect from the previously described functions.

The device is designed for continuous biometric recognition and, as such, it can be used to control the access to physical facilities or any other operations in which the proof of the identity of the user is convenient or necessary either in a continuous or momentary way.

The invention can be better understood through the analysis of the corresponding drawings, some of which illustrate preferential embodiments.

FIG. 1 illustrates the typical representation of an ECG signal during a heartbeat cycle. Part of the representative information of the signal is: the P instant, which corresponds to the activation of the sinoatrial node (the natural pacemaker of the body which triggers the heartbeat); the QRS instants, which correspond to the contraction of the heart due to the depolarization of the muscular fibers; and the T instant, which corresponds to the relaxation of the cardiac muscle by effect of the muscle fibers repolarization.

The ECG signal can also be characterized by the raw data itself as collected by the sensory unit (205), or by representative latency and amplitude information extracted from notable points within the raw data (e.g. the elapsed time between the P and R instants—PR—, between the S and T instants—ST—, etc.), by a combination of both, or also by another type of parameters or alternative representations (e.g. Fast Fourier Transform—FFT—, Discrete Cosine Transform—DCT—or Wavelets).

FIG. 2 illustrates the block diagram, depicting the main modules of the device for continuous biometric recognition based on electrocardiographic signals. Depending on the preferred embodiment, the signal measured from the electronic module of measurement terminals (201), feeds the electronic module of signal transduction and conditioning with virtual ground (202) that performs the filtering and amplification of the signals, which in turn are transformed by the electronic module of analog-to-digital conversion (203) into a representation manageable in the computational unit (206). The signals are then passed by an electronic module of signal transmission (204) and sent to the computational unit (206), that produces a result about the biometric recognition of the user. The electronic module of measurement terminals (201) can be particularized as capacitive contactless sensors integrated in the shell of a tablet computer (403), in the seat of a car (304) or (305), in the seat of a motorcycle (504), or in the structure of a gym machine (603). The electronic module of measurement terminals (201) can also be particularized in non-metallic conductive elements integrated in the steering wheel of a car (303) or in the handlebars of a motorcycle (503).

FIGS. 3a), 3b) and 3c) illustrate a schematic view of one of the preferential embodiments of the present invention where the continuous biometric recognition is performed in the cabin of a car, in which the sensory unit (205) is integrated in the car seat, in a setup that does not require direct contact with the body of the user. The electronic module of measurement terminals without contact with the body of the user, items (304) and (305), are capacitive sensors from the sensory unit (205) that are integrated in the textile cover or in the seat structure itself, and which in this case operate without any direct contact with the body of the user. The signals are measured from any combination of the available elements when the user sits in the car as illustrated in FIG. 3b). In an alternative configuration, the electronic module of measurement terminals (201) and the sensory unit (205) can be integrated in the steering wheel of a car, such as illustrated by the pair of non-metallic conductive elements (303), and in this case the measurement is performed when the user places his/her hands in the steering wheel without the need to measure the common mode voltage of the body (real ground), as illustrated by FIG. 3c). The measurement terminals are preferably of non-metallic materials, such as conductive coatings, films or adhesives. Regardless of the configuration of the sensory unit (205), it captures the ECG signal using the electronic module of measurement terminals, in this case embodied by the non-metallic conductive elements (303) integrated in the steering wheel or capacitive contactless sensors integrated in the seat of a car (304) or (305), amplifies the signal and performs its conditioning and analog-to-digital conversion allowing the transmission to the central console of a car (301). The transmission can be performed through a wireless channel, through the CAN bus of the vehicle, or through any other type of connection that allows it to reach the central console of the car or any other subsystem of the car in charge of the process performed by the computational unit (206) (pre-processing, extraction of the representative pattern and identification or verification of the identity of the user). In this scenario, a graphical representation of the signals and/or the decision produced by the biometric recognition system can be presented in the central processing unit of a car (301). Depending on the result produced by the biometric recognition system, the vehicle can automatically adjust its setting to the individual preferences of the user (e.g. radio stations; the list of personal contacts in the agenda of the vehicle; the position of the steering column, seats and mirrors; maximum speed allowed; among others), or limit it's functions according to the perceived user (including inhibition to use the vehicle when an impostor is detected). In the case where the sensory unit (205) is integrated in the steering wheel, the system can also provide information of whether the user has his hands in the steering wheel or not, information which can be used for accident prevention purposes.

FIGS. 4a) and 4b) illustrate a schematic view of another preferential embodiment of the present invention, in which the sensory unit (205) has a contactless capacitive sensor integrated in the shell of a tablet computer (403), which corresponds to the electronic module of measurement terminals (201). In this configuration, there is no direct contact between the device and the user; there is only the electronic module of measurement terminals (201), which is enclosed inside the structure of the tablet computer, enabling the acquisition of ECG signals through a capacitive method, without changing the external appearance of the tablet computer, and eliminating the need for a direct contact between the device and the user. When the user places his hands in the vicinity of the electronic module of measurement terminals (201), the device will measure the ECG for biometric recognition purposes.

The electronic module of measurement terminals (201) is sensitive both in the front and back of the device, but also in other configurations that enable the acquisition of ECG signals based solely on the proximity of the user to the device but with no direct contact, whether it is performed by metallic on non-metallic elements. In this embodiment the sensory unit (205) is integrated in, and communicates directly with, the computational unit (206) through the standard communication interfaces. Using the acquired data, a graphical representation of the signals or of the decision results can be presented in the graphical representation screen of a tablet computer (402) that the computation unit (206) has for such purpose. As in the previous embodiment, the result of the biometric recognition can be used to adjust the preferences of the user (e.g. e-mail accounts; list of personal contacts; background images, audio alerts, ring tones and colors; the visible or installed applications; the appearance and navigation of the screens; the language and locale settings; the internet connectivity settings; among others) or limit the access to some of the functions of the device or to digital resources accessed through it (e.g. login, payments, Internet websites, files, among others).

FIGS. 5a) and 5b) illustrate a schematic view of another preferred embodiment of the present invention, in which the sensory unit (205) is integrated in the seat of a motorcycle, in a setting that does not require direct contact with the body of the user. The electronic module of measurement terminals (201) corresponds to contactless capacitive sensors, integrated in the seat of a motorcycle (504), which are elements of the sensory unit (205) that work without direct contact with the user and are integrated in the cover or in the structure of the seat itself. The signals are measured through any combination of the available elements when the user seats on the motorcycle. In an alternative configuration, the electronic module of measurement terminals (201) of the sensory unit (205) can be integrated in the handlebars of the motorcycle (503), as illustrated by the non-metallic materials in the handlebars of a motorcycle (503), in which case the measurement is performed when the user places his hands on the handlebars, without the need to measure the common mode voltage of the body (real ground). Preferably, the electronic module of measurement terminals (201) is made of a non-metallic material such as conductive coatings, films or adhesives. Regardless of the configuration of the sensory unit (205) it acquires the ECG signal using the electronic module of measurement terminals, in this case embodied by non-metallic conductive elements integrated in the handlebars of a motorcycle (503) or contactless capacitive sensors integrated in the seat of a motorcycle (504), amplifies the signal, and performs its conditioning and analog-to-digital conversion in order to allow its transmission to the central processing unit of the central console of the motorcycle (501). The transmission can be performed through a wireless channel, through the CAN bus of the vehicle, or through any other type of connection, to the dials or any other subsystem of the motorcycle that can perform the tasks of the central processing unit of the motorcycle (501) (pre-processing, extraction of the representative patterns and identification or authentication of the user). In this scenario, a graphical representation of the signal and/or the decision produced by the biometric recognition system can be presented in the graphical representation screen of the central console of the motorcycle (502). According to the result produced by the biometric recognition system, the vehicle can automatically adjust its setting to the individual preferences of the user (e.g. the maximum allowed speed; the maximum power; among others), or limit its functions according to the perceived user (including preventing the use when an impostor is detected). When the sensory unit (205) is integrated in the handlebars, it can also be used to detect whether the user has both hands on the handlebars, an information that can be used for accident prevention purposes.

FIGS. 6a) and 6b) illustrate a schematic view of another preferential embodiment of the present invention, in which the sensory unit (205) is integrated in a gym machine, in a setting where the electronic module of measurement terminals (201) from the sensory unit (205) is integrated in the structure of the machine, as illustrated by the contactless capacitive sensors integrated in the structure of a gym machine (603), in which case the measurement is performed without direct contact with the body of the user. The ECG signal is acquired using the capacitive sensors integrated in the structure of a gym machine (603), amplified, conditioned and converted from analog to digital format, allowing its transmission to the central processing unit of the gym machine (601). The transmission can be performed using a wireless channel, through wires placed inside the structure of the machine, or through any other kind of connection to the central processing unit of the gym machine (601), and subsequently to the screen on the central console of the gym machine (602) or any other subsystem of the machine that performs the tasks of the central processing unit of the gym machine (601) (pre-processing, extraction of the representative pattern, and identification or verification of the identity of the user). In this scenario, a graphical representation of the signals and/or the decision on the identity of the user produced by the biometric recognition system can be presented in the screen of the central console of the gym machine (602).

Depending on the result produced by the biometric recognition system, the machine can automatically adjust its settings to the individual preferences of the user (e.g. training program; duration of the exercise; position of the work platform; among others), limit the functions of the machine according to the perceived user (e.g. maximum speed, work load, etc.), or record and associate the performance indicators to the corresponding user (e.g. duration of the exercise; intensity of the training program; maximum speed achieved; burned calories; among others).

EXAMPLES

Figure 1:
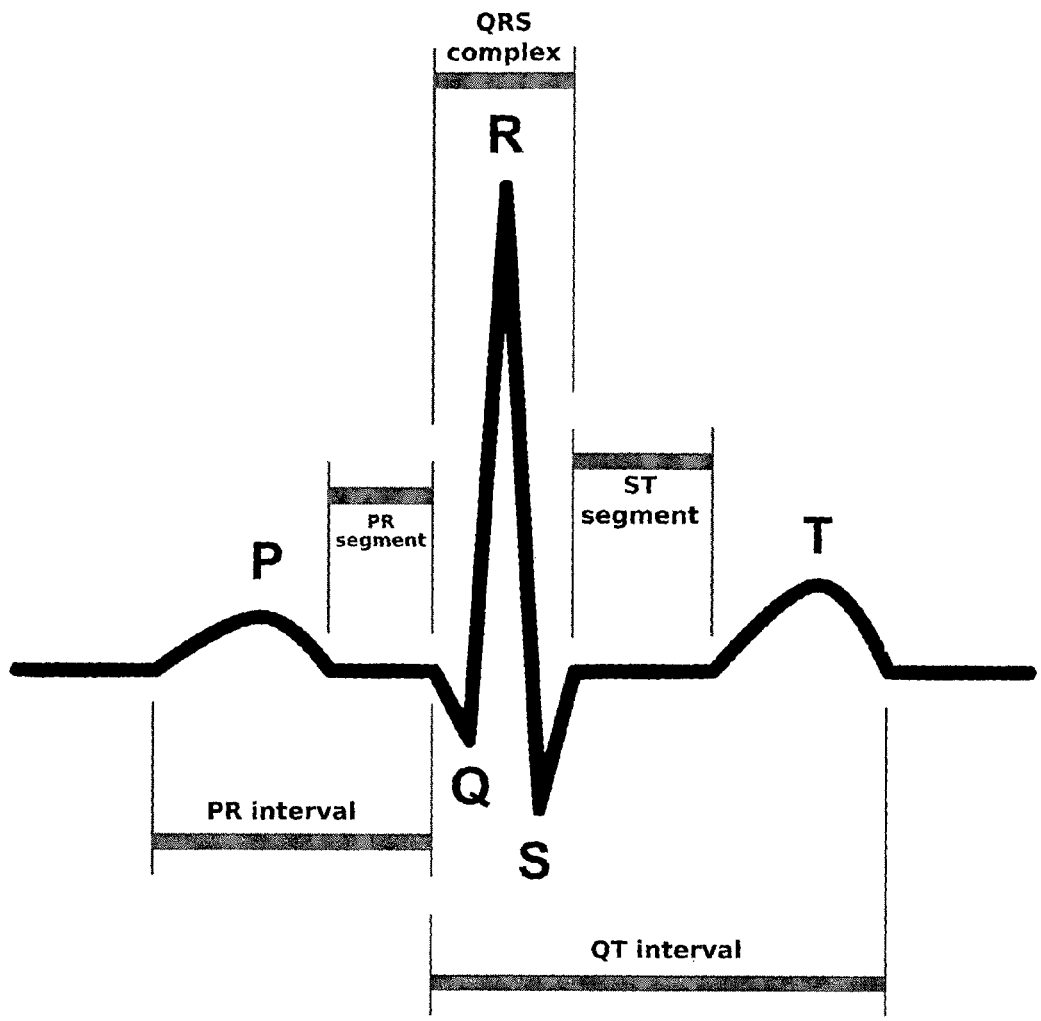
FIG. 1 shows a typical representation of the ECG signal during a heartbeat cycle.
Figure 2:
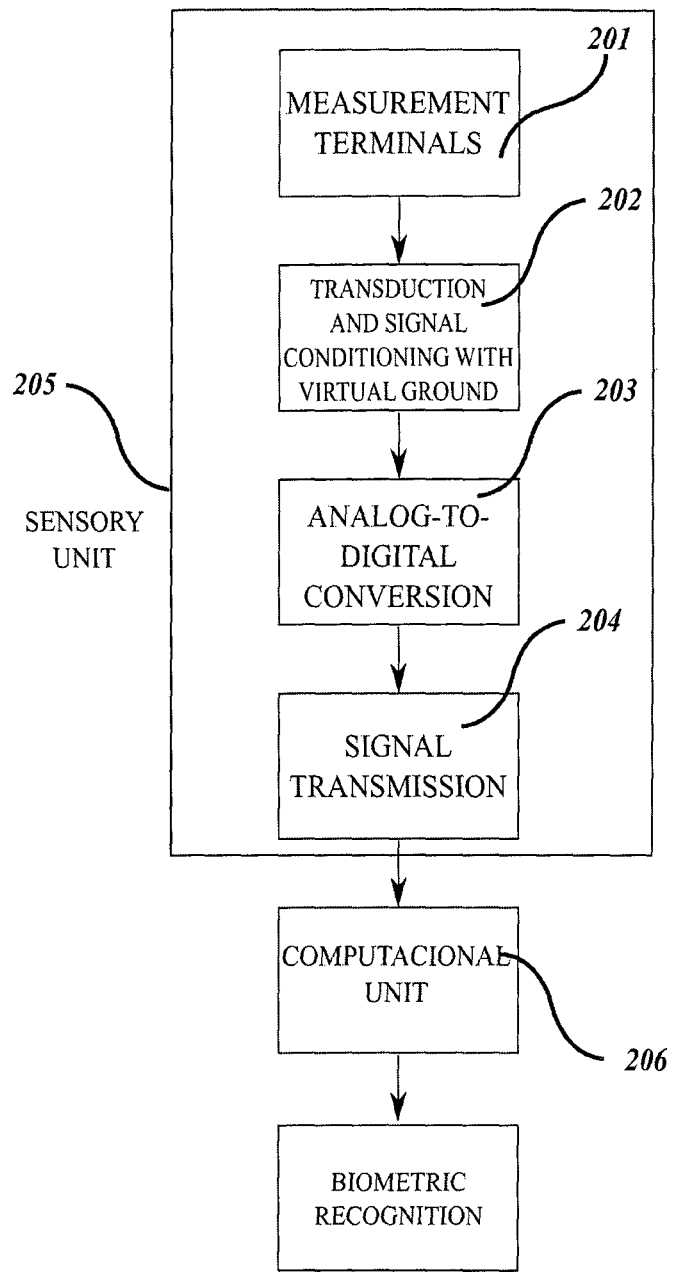
FIG. 2 represents a block diagram showing the modules of the device for continuous biometric recognition based on electrocardiographic signals.
Figure 3A:
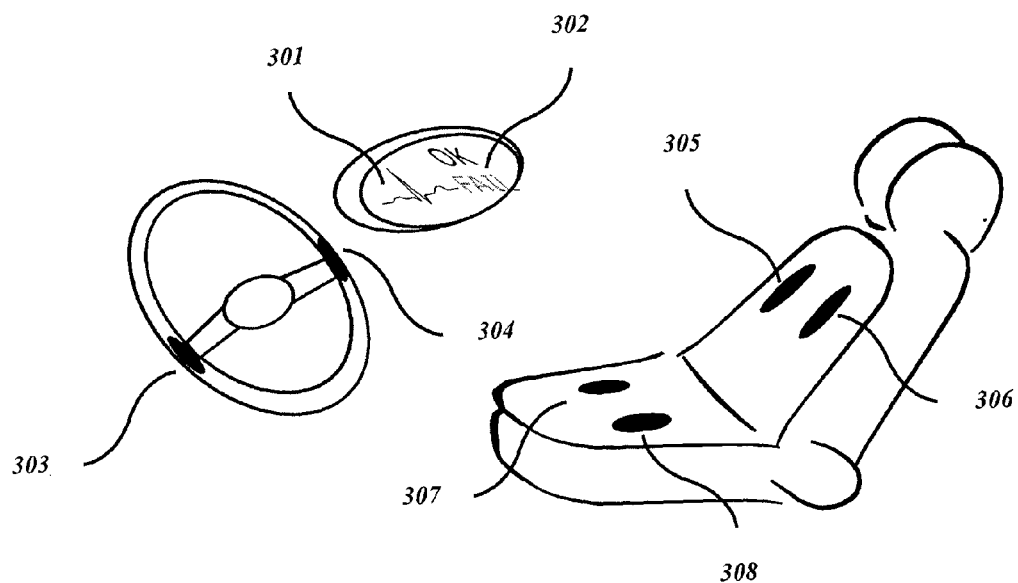
FIG. 3a) represents a schematic view of one of the preferential embodiments of the invention, in which the device is integrated in the cabin of a car. In this case the sensory unit (205) has the electronic module of measurement terminals (201), embodied by non-metallic conductive elements (303) integrated in the steering wheel of the car and/or contactless capacitive sensors integrated in the seat of the car (304) and (305). The signal acquired by the sensory unit (205) is transmitted to the central processing unit of a car (301) and either the signal or the result of the biometric recognition process can be represented in the central console of the car (302).
Figure 3B:
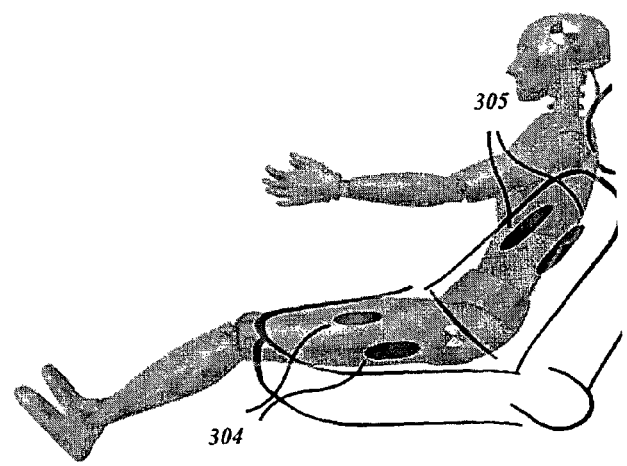
FIG. 3b) represents a schematic view of a contactless measurement of the signal in a user, where the sensory unit (205) has the electronic module of measurement terminals (201) embodied in contactless capacitive sensors integrated in the seat of a car (304) and (305).
Figure 3C:
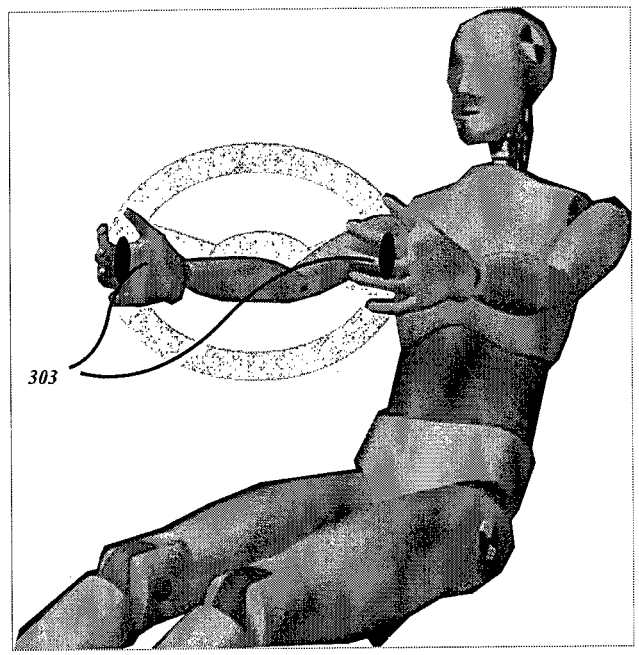
FIG. 3c) represents a schematic view of the signal acquisition in a user with direct contact with his/her body, from a sensory unit (205) where the electronic module of measurement terminals (201) is embodied by non-metallic conductive elements integrated in the steering wheel of a car (303).
Figure 4A:
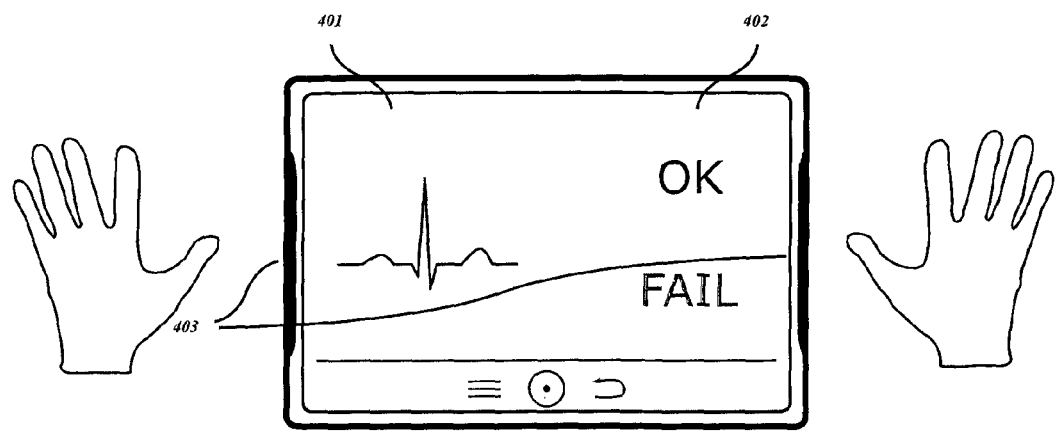
FIG. 4a) represents a schematic frontal view of another possible embodiment of the invention, in which the sensory unit (205) is integrated in the shell of a tablet computer, and the acquisition is performed with the electronic module of measurement terminals (201) embodied by contactless capacitive sensors integrated in the shell of the table computer (403).
Figure 4B:
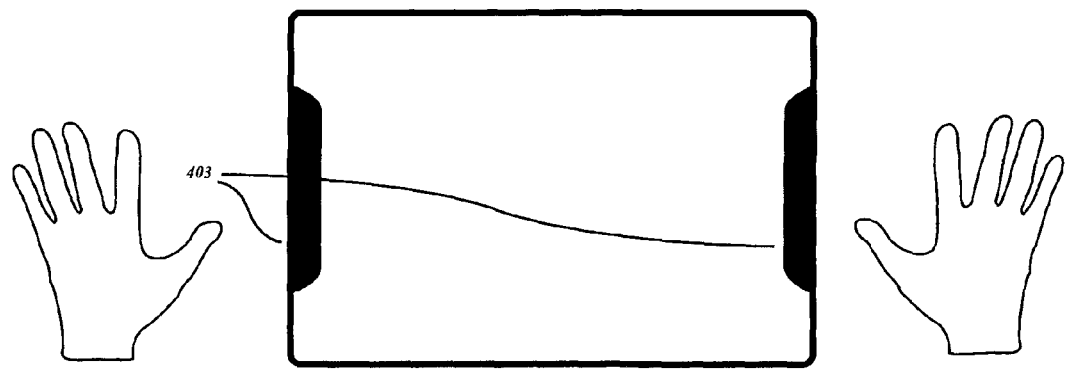
FIG. 4b) represents a schematic back view of another possible embodiment of the invention, in which the sensory unit (205) is integrated in the shell of the tablet computer and the acquisition is performed using the electronic module of measurement terminals (201) embodied by contactless capacitive sensors integrated in the shell of the tablet computer (403).
Figure 5A:
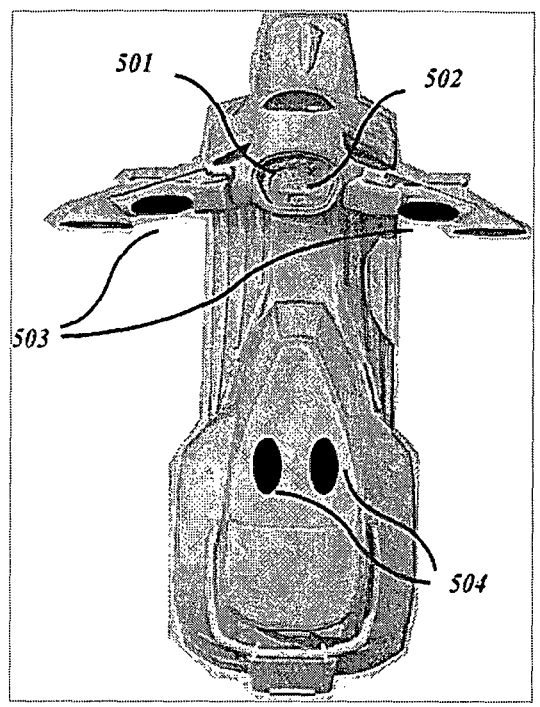
FIGS. 5a) and 5b) represent a schematic view of another embodiment of the invention, in which the sensory unit (205) has an electronic module of measurement terminals (201) embodied by non-metallic conductive elements integrated in the handlebars of a motorcycle (503) and/or by contactless capacitive sensors integrated in the seat of a motorcycle (504). The computational unit (206) is integrated in the central processing unit of the central console of the motorcycle (501), and the result of the biometric recognition process can be shown in the graphical representation screen of the central console of the motorcycle (502).
Figure 5B:
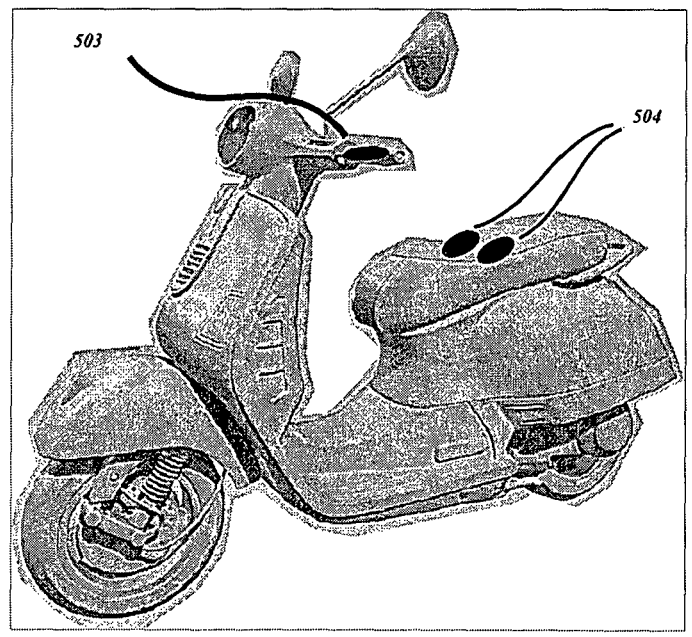
Figure 6A:
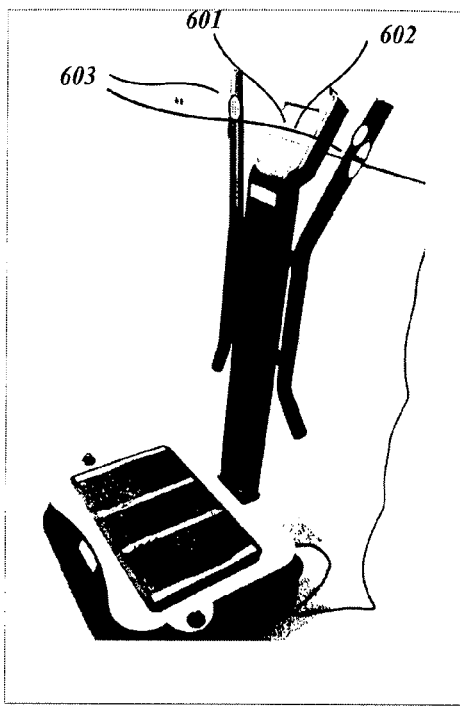
FIGS. 6a) and 6b) represent a schematic view of an embodiment of the invention, in which the sensory unit (205) has an electronic module of measurement terminals (201) embodied by contactless capacitive sensors, integrated in the structure of a gym machine (603), and where the computational unit (206) is the central processing unit on the console of the gym machine (601), considered to be an electronic device, of the screen on the central console of a gym machine (602).
Figure 6B:
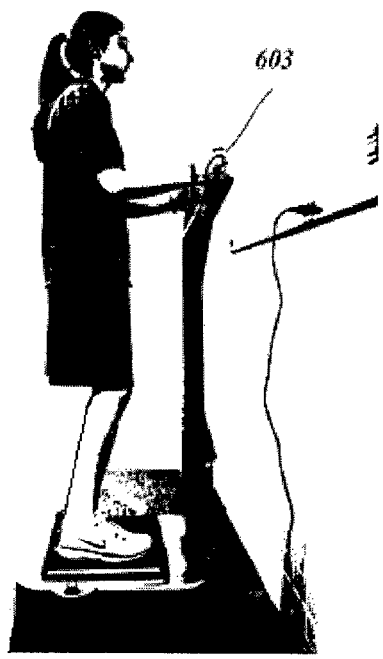

In one of the preferred embodiments of the present invention, the sensory unit (205) is enclosed on a tablet computer, which also works as the computational unit (206). In this embodiment, the tablet computer has a contactless capacitive sensor integrated in the shell of the tablet computer (403), with measurement zones in the side and back panels of the tablet computer. These zones are connected to the electronic module of signals transduction and conditioning with virtual ground (202), that amplifies and filters the signals, in such way that it allows the measurement of the ECG signal whenever the user places his/her hands in the vicinity of the measurement zones, always without the need for direct contact between the user and the device. In this embodiment, the electronic module of signal transmission (204) between the sensory unit (205) and the computational unit (206) transmits the signal through the motherboard of the tablet computer, using tacks in the printed circuit board of the device, or connection pins with the conventional communication interfaces of the tablet device (COM port, USB interface, or even GPIO pins).

In another preferred embodiment of the present invention, the sensory unit (205) is integrated in the steering wheel or seat of a car, the computational unit (206) being the central processing unit of the vehicle. In this embodiment the sensory unit (205) uses one or several capacitive sensors integrated in the seat of the car (304) and (305), allowing the ECG to be acquired without contact with the body of the user, although it can also use non-metallic conductive elements integrated in the steering wheel of a car (303), allowing the ECG to be acquired with contact, while the user is inside the vehicle. The electronic module of signal transmission (204) includes a device for wireless connectivity integrated in the sensory unit (205), or a module for communication through the CAN bus of the car.

In another preferred embodiment of the present invention, the sensory unit (205) is integrated in the handlebars or seat of a motorcycle, in which case the computational unit (206) is the processing unit on the central console of the motorcycle (501). In this embodiment, the sensory unit (205) uses one or more capacitive sensors integrated in the seat of the motorcycle (504), allowing the ECG to be acquired without contact with the user, although it can also use non-metallic conductive elements integrated in the handlebars of the motorcycle (503), enabling the ECG to be acquired with contact, when the user is sitting on the motorcycle. The electronic module for signal transmission (204) has a module for cabled communication, or a module for communication through the CAN bus of the motorcycle and is integrated in the sensory unit (205).

In yet another preferred embodiment of the present invention, the sensory unit (205) is integrated in a gym machine, the computational unit (206) is the central processing unit on the central console of the gym machine (601), and the result of the biometric identification process can be presented on the screen of the center console of the gym machine (602), considered to be an electronic device. In this embodiment the machine uses a capacitive sensor integrated in the structure of the gym machine (603), allowing the ECG to be acquired without contact while the user is operating the machine. The electronic module of signal transmission (204) uses a cabled connection to transmit the data from the sensory unit (205) to the central processing unit on the central console of the gym machine (601) or to the screen on the central console of the gym machine (602).

In any of the previously described embodiments, the ECG can be acquired as an external accessory. In the configuration where it is an external accessory, a preferred embodiment of the present invention has the sensory unit (205) integrated in an office chair, and the computational unit (206) is the central processing unit of a computer. In this embodiment, the sensory unit (205) uses one or more capacitive elements, enabling the ECG to be acquired without contact, while the user is sitting in the chair and working with the computer. The electronic module of signal transmission (204) uses a module for wireless communication to transmit the data from the sensory unit (205) via Bluetooth, WiFi, ZigBee, ANT or any other protocol that allows wire-free communication.

In any of the embodiments previously described, the computational unit (206) executes a set of pattern recognition algorithms that match the acquired ECG signals and related representative information, to the patterns previously stored during the enrollment phase for the registered users. For illustrative purposes, in the scope of the described embodiments, the biometric recognition is performed through a nearest neighbor algorithm (k-NN) the Euclidean distance as similarity metric, although other approaches are also possible.

Without loss of generality due to the fact that a detailed description of the invention was disclosed, its preferred embodiments should not constitute a limitation to the overreach of the invention. In this sense, not only other variations of the preferred embodiments are admissible, but also all other embodiments that share the claimed characteristics are considered to belong to the scope of the present invention.

REFERENCES

1. Kyoso, M.; Uchiyama, A. "Development of an ECG Identification System". Proceedings of the 23rd Annual International Conference of the IEEE Engineering in Medicine and Biology Society. 2001.
2. Biel, L.; Pettersson, O.; Philipson, L.; Wide, P. "ECG Analysis: A New Approach in Human Identification". IEEE Transactions on Instrumentation and Measurement Journal, Vol. 50, N. 3. 2001.

3. Lourenço, A.; Silva, H.; Fred, A. "Unveiling the Biometric Potential of Finger-Based ECG Signals". Computational Intelligence and Neuroscience, Vol. 2011. 2011.
4. Silva, H.; Lourenço, A.; Fred, A.; Filipe, J. "Clinical Data Privacy and Customization via Biometrics Based on ECG Signals". Proceedings of the Conference Information Quality in eHealth—USAB. 2011.
5. Silva, H.; Lourenço, A.; Lourenço, R.; Leite, P.; Antão, D; Fred, A. "Study and Evaluation of a Single Differential Sensor Design Based on Electro-textile Electrodes for ECG Biometrics Applications". Proceedings of the IEEE Sensors Conference. 2011.
6. Sriram, J.; Shin, M.; Choudhury, T.; Kotz, D. "Activity-aware ECG-based Patient Authentication for Remote Health Monitoring". Proceedings of the 2009 edition of the ICMI-MLMI Conference. 2009.

The invention claimed is:

1. A device for continuous biometric recognition using electrocardiographic signals comprising:
    measurement terminals comprising capacitive sensors for continuous measurement of the electrocardiographic signal or non-metallic conductive elements for the measurement of electrical potential differential, or mechanical elements;
    an electronic transduction and signal conditioning; circuit including a virtual ground, and an electromagnetic noise filter, the electronic transduction and signal conditioning circuit receiving the electrocardiographic signals and filtering the electrocardiographic signals in the electromagnetic noise filter to provide the electrocardiographic signals free of external noise;
    electronic equipment for digital processing the received filtered electrocardiographic signals, generating biometric recognition of a user and customizing of settings of the electronic equipment according to a result of the biometric recognition of the user, wherein the biometric recognition of the user occurs uninterruptedly while the device is being used.

2. The device for continuous biometric recognition using electrocardiographic signals according to claim 1, the device adapted to be used inside a cabin of a car, wherein
    the capacitive sensors for continuous measurement of the electrocardiographic signals are integrated in a steering wheel of the car by non-metallic conductive elements;
    the capacitive sensors for continuous measurement of the electrocardiographic signals are integrated in a seat of the car by contactless capacitive sensors;
    the electronic equipment is a central processing unit of a central console of the car and a screen of the central console of the car; and
    the electronic equipment includes a method for communication with a CAN bus of the car.

3. The device for continuous biometric recognition using electrocardiographic signals according to claim 1, the device adapted to be used on a motorcycle, wherein
    the capacitive sensors for continuous measurement of the electrocardiographic signals are integrated in handlebars of the motorcycle by non-metallic conductive elements;
    is the capacitive sensors for continuous measurement of the electrocardiographic signals are integrated in a seat of the motorcycle by contactless capacitive sensors;
    the electronic equipment is a central processing unit on a central console of the motorcycle and graphical representation screen on a central console of the motorcycle; and
    the electronic equipment includes a method for communication with a CAN bus of the motorcycle.

4. The device for continuous biometric recognition using electrocardiographic signals according to claim 1, adapted to be used on a gym machine, wherein:
    the capacitive sensors for continuous measurement of the electrocardiographic signals are integrated in a structure of the gym machine by contactless capacitive sensors; and
    the electronic equipment is a central processing unit of a central console of the gym machine and a screen of the central console of the gym machine.

5. The device for continuous biometric recognition using electrocardiographic signals according to claim 1, the device adapted to be used on a tablet computer, wherein
    the capacitive sensors for continuous measurement of the electrocardiographic signals are integrated in a shell of a tablet computer by contactless capacitive sensors and a mother board of the tablet; and
    the electronic equipment is a central processing unit of the tablet computer and a graphical representation screen of the tablet computer.

6. The device for continuous biometric recognition according to claim 2 wherein the non-metallic elements are conductive coatings, films or adhesives.

7. The device for continuous biometric recognition according to claim 1, wherein the measurement terminals are capacitive sensors or piezoelectric sensors.

8. The device for continuous biometric recognition according to claim 1, wherein the capacitive sensors for continuous measurement of the electrocardiographic signals are integrated in the electronic equipment.

9. The device for continuous biometric recognition according to claim 1, wherein the capacitive sensors for continuous measurement of the electrocardiographic signals are separated from the electronic equipment.

10. A method for continuous biometric recognition from electrocardiographic signals, using the device defined in claim 1, comprising the following steps:
    a) continuous acquisition of the electrocardiographic signals through the capacitive sensors for continuous measurement of the electrocardiographic signals;
    b) transduction and signal conditioning with the virtual ground and the electromagnetic noise filter that measures the electrocardiographic signals using one or more measurement terminals, filters and amplifies the electrocardiographic signals;
    c) signal conversion through the use of an analog-to-digital signal conversion that integrates a quantization element and an analog-to-digital converter, that transforms physical quantities corresponding to the electrocardiographic signals into a digital representation;
    d) transmission of the electrocardiographic signals acquired by the capacitive sensors for continuous measurement of the electrocardiographic signals to the electronic equipment;
    e) processing the electrocardiographic signals and extracting representative information related with identity of the user in the electronic equipment;
    f) recording of the representative information of the user in a database that is integrated or not in the electronic equipment;
    g) classification of the representative information of the user; and
    h) decision on the biometric recognition of the user in the electronic equipment.

* * * * *